(12) United States Patent
Jain et al.

(10) Patent No.: US 8,816,072 B2
(45) Date of Patent: Aug. 26, 2014

(54) PROCESS FOR THE PREPARATION OF CRYSTALLINE APREPITANT HAVING FORM I CONTENT

(75) Inventors: Deepak Mohanlal Jain, Surat (IN); Maneck Khurana, New Delhi (IN); Hiten Sharadchandra Mehta, Ahmedabad (IN); Abhay Tatiya, Aurangabad (IN); Asok Nath, Gurgaon (IN); Sanjay Mahadeo Gade, Solapur (IN); Mohan Prasad, Gurgaon (IN); Subhash Dhar, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 437 days.

(21) Appl. No.: 13/375,548

(22) PCT Filed: Jun. 2, 2010

(86) PCT No.: PCT/IB2010/052471
§ 371 (c)(1),
(2), (4) Date: Jul. 13, 2012

(87) PCT Pub. No.: WO2010/140132
PCT Pub. Date: Dec. 9, 2010

(65) Prior Publication Data
US 2012/0277426 A1 Nov. 1, 2012

(30) Foreign Application Priority Data
Jun. 2, 2009 (IN) .......................... 1128/DEL/2009

(51) Int. Cl.
*C07D 413/06* (2006.01)

(52) U.S. Cl.
USPC ...................................... 544/132

(58) Field of Classification Search
USPC ......................................... 544/132
See application file for complete search history.

(56) References Cited

U.S. PATENT DOCUMENTS

| 5,719,147 A | 2/1998 | Dorn et al. ................. 514/227.5 |
| 6,096,742 A | 8/2000 | Crocker et al. ............... 514/241 |
| 6,583,142 B2 | 6/2003 | Crocker et al. ............... 514/241 |

FOREIGN PATENT DOCUMENTS

| WO | WO 2007/016582 | 2/2007 | ......... A61K 31/5377 |
| WO | WO 2007/039883 | 4/2007 | ........... C07D 413/06 |
| WO | WO 2007/044829 | 4/2007 | ............. A01N 43/00 |
| WO | WO 2007/088483 | 8/2007 | ........... C07D 413/06 |
| WO | WO 2007/112457 | 10/2007 | ......... A61K 31/5377 |
| WO | WO 2007/147160 | 12/2007 | ................ A61K 9/00 |
| WO | WO 2008/026216 | 3/2008 | ........... C07D 413/06 |
| WO | WO 2008/044102 | 4/2008 | ........... C07D 413/06 |
| WO | WO 2008/104512 | 9/2008 | ........... C07D 413/06 |
| WO | WO 2009/001203 | 12/2008 | ........... C07D 265/32 |

OTHER PUBLICATIONS

Helmy et al., "Characterization and Quantitation of Aprepitant Drug Substance Polymorphs by Attenuated Total Reflectance Fourier Transform Infrared Spectroscopy", *Analytical Chemistry*, 75(3):605-611 2003.

*Primary Examiner* — Rebecca Anderson

(57) ABSTRACT

The present invention provides a process for preparation of crystalline aprepitant having not more than 15% by weight of Form I content which comprises, a) dissolving aprepitant in a suitable solvent to obtain a solution, b) cooling the solution to 10-15° C., c) optionally seeding the solution with aprepitant Form I crystals, d) adding an anti-solvent to the solution, and e) isolating crystalline aprepitant having not more than 15% by weight of Form I content.

14 Claims, 4 Drawing Sheets

FIGURE 1A

| Pos. [°2Th.] | FWHM [°2... | Area [cts*°2Th.] | d-spacing [Å] | Height [cts] | Rel. Int. [%] |
|---|---|---|---|---|---|
| 4.1727 | 0.1506 | 34.26 | 21.17637 | 230.66 | 1.92 |
| 8.2613 | 0.1506 | 64.16 | 10.70287 | 432.01 | 3.59 |
| 12.1462 | 0.1004 | 29.88 | 7.28691 | 301.82 | 1.67 |
| 12.7081 | 0.1840 | 255.25 | 6.96399 | 1406.24 | 14.29 |
| 13.5513 | 0.2007 | 58.19 | 6.53435 | 283.84 | 3.28 |
| 14.5353 | 0.1673 | 81.13 | 6.09483 | 491.67 | 4.54 |
| 15.3648 | 0.2007 | 75.02 | 5.76698 | 378.87 | 4.20 |
| 16.2392 | 0.1840 | 290.07 | 5.45834 | 1598.05 | 16.24 |
| 16.8550 | 0.1171 | 213.80 | 5.26828 | 1850.93 | 11.97 |
| 17.2774 | 0.1840 | 539.62 | 5.13264 | 2972.86 | 30.21 |
| 17.6566 | 0.1004 | 83.78 | 5.02325 | 644.21 | 3.57 |
| 18.1357 | 0.1506 | 234.43 | 4.89161 | 1578.55 | 13.12 |
| 18.7435 | 0.3007 | 78.43 | 4.73434 | 396.08 | 4.39 |
| 19.4294 | 0.3007 | 79.80 | 4.56872 | 402.98 | 4.47 |
| 20.2473 | 0.1840 | 627.99 | 4.38397 | 3459.73 | 35.15 |
| 20.7401 | 0.2007 | 830.91 | 4.28288 | 4196.25 | 46.51 |
| 21.3133 | 0.1840 | 608.62 | 4.16839 | 3352.99 | 34.07 |
| 21.9337 | 0.1673 | 90.01 | 4.05242 | 545.45 | 5.04 |
| 22.9801 | 0.2676 | 920.70 | 3.87021 | 3487.22 | 51.54 |
| 24.0243 | 0.2508 | 738.07 | 3.70430 | 2981.86 | 41.33 |
| 24.9258 | 0.2676 | 1786.39 | 3.57234 | 6766.07 | 100.00 |
| 26.7519 | 0.2007 | 326.62 | 3.33249 | 1649.44 | 18.28 |
| 27.7267 | 0.1506 | 202.11 | 3.21751 | 1360.90 | 11.31 |
| 29.1334 | 0.2342 | 204.26 | 3.06577 | 884.18 | 11.43 |
| 30.6162 | 0.2007 | 160.94 | 2.92011 | 812.77 | 9.01 |
| 31.5830 | 0.2676 | 176.63 | 2.83298 | 669.81 | 9.89 |
| 31.9635 | 0.1004 | 68.10 | 2.80083 | 687.79 | 3.81 |
| 33.4280 | 0.2676 | 114.43 | 2.68220 | 433.50 | 6.41 |
| 34.3747 | 0.2007 | 93.60 | 2.60895 | 472.70 | 5.24 |
| 35.5959 | 0.3346 | 286.62 | 2.52219 | 868.47 | 16.04 |
| 37.7899 | 0.2342 | 205.04 | 2.38065 | 887.55 | 11.48 |
| 38.7547 | 0.3346 | 295.72 | 2.32358 | 896.64 | 16.55 |

FIGURE 2A

| Pos. [°2Th.] | FWHM [°2...] | Area [cts*°2Th.] | d-spacing [Å] | Height [cts] | Rel. Int. [%] |
|---|---|---|---|---|---|
| 3.1465 | 0.1338 | 1.70 | 28.08012 | 12.88 | 0.13 |
| 4.2152 | 0.1338 | 38.43 | 20.96295 | 291.08 | 2.95 |
| 8.3736 | 0.1338 | 86.12 | 10.55953 | 652.36 | 6.71 |
| 12.4963 | 0.1338 | 95.42 | 7.08347 | 722.83 | 7.43 |
| 12.7717 | 0.1338 | 123.10 | 6.93143 | 932.48 | 9.59 |
| 13.5345 | 0.2342 | 49.63 | 6.54242 | 214.83 | 3.87 |
| 14.5884 | 0.1171 | 44.85 | 6.07548 | 388.39 | 3.49 |
| 15.3427 | 0.2342 | 92.49 | 5.77522 | 400.37 | 7.28 |
| 16.3254 | 0.1840 | 208.97 | 5.42973 | 1151.25 | 16.28 |
| 16.9470 | 0.1506 | 157.78 | 5.23194 | 1062.38 | 12.29 |
| 17.3293 | 0.1840 | 367.75 | 5.11738 | 2026.00 | 28.64 |
| 18.2266 | 0.1673 | 147.95 | 4.86742 | 896.38 | 11.52 |
| 18.8323 | 0.2007 | 62.66 | 4.71222 | 333.57 | 5.11 |
| 20.2873 | 0.1171 | 299.41 | 4.37849 | 3592.11 | 23.32 |
| 20.8531 | 0.1673 | 591.80 | 4.25992 | 3586.91 | 46.10 |
| 21.2731 | 0.1338 | 302.05 | 4.17674 | 2288.64 | 23.53 |
| 21.9773 | 0.2676 | 117.03 | 4.04448 | 443.25 | 9.12 |
| 23.8684 | 0.2676 | 722.32 | 3.85692 | 2735.44 | 56.25 |
| 24.6982 | 0.2342 | 559.75 | 3.60311 | 2422.95 | 43.60 |
| 25.0446 | 0.1840 | 1283.85 | 3.55566 | 7072.96 | 100.00 |
| 26.8220 | 0.2175 | 314.52 | 3.32394 | 1466.19 | 24.50 |
| 27.8079 | 0.2676 | 310.59 | 3.20830 | 1176.38 | 24.10 |
| 29.2264 | 0.1506 | 141.21 | 3.05573 | 950.83 | 11.00 |
| 30.7519 | 0.3011 | 202.68 | 2.90755 | 682.35 | 15.79 |
| 31.6245 | 0.3346 | 214.60 | 2.82927 | 650.25 | 16.72 |
| 32.0972 | 0.2997 | 105.41 | 2.78868 | 507.10 | 7.82 |
| 33.4156 | 0.2676 | 117.76 | 2.68160 | 446.82 | 9.17 |
| 35.7023 | 0.3011 | 250.06 | 2.51492 | 841.90 | 19.48 |
| 37.8537 | 0.3346 | 307.44 | 2.37679 | 931.57 | 23.95 |
| 38.8281 | 0.3011 | 294.87 | 2.31936 | 992.75 | 22.97 |

PROCESS FOR THE PREPARATION OF CRYSTALLINE APREPITANT HAVING FORM I CONTENT

FIELD OF THE INVENTION

The present invention relates to a process for preparation of crystalline aprepitant having not more than 15% by weight of Form I content.

BACKGROUND OF THE INVENTION

Aprepitant of Formula I is a substance P/neurokinin 1 (NK1) receptor antagonist, chemically described as 5-[[(2R, 3S)-2-[(1R)-[3,5-bis(trifluoromethyl)phenyl]ethoxy]-3-(4-fluorophenyl)-4-morpholinyl]methyl]-1,2-dihydro-3H-1,2, 4-triazol-3-one and in combination with other antiemetic agents, is indicated for the prevention of acute and delayed nausea and vomiting associated with initial and repeat courses of highly emetogenic cancer chemotherapy including high-dose cisplatin and prevention of nausea and vomiting associated with initial and repeat courses of moderately emetogenic cancer chemotherapy. Aprepitant is also indicated for the prevention of postoperative nausea and vomiting.

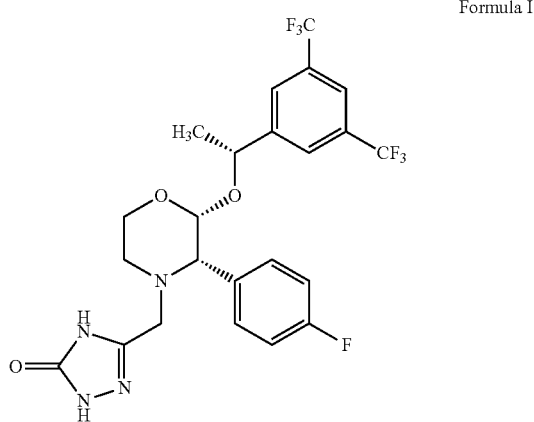 [SMILES: C[C@@H](O[C@H]1OCCN(Cc2n[nH]c(=O)[nH]2)[C@H]1c1ccc(F)cc1)c1cc(C(F)(F)F)cc(C(F)(F)F)c1]

Formula I

U.S. Pat. No. 5,719,147 provides a process for the preparation of aprepitant in a mixture of Form I and Form II which involves dissolving crude aprepitant in hot methanol, adding charcoal, then filtering, and washing the charcoal with hot methanol, cooling the methanol solution to room temperature, and then adding water drop wise. After being stirred at room temperature for 2 hours, the suspension is filtered to isolate the purified product as a white crystalline compound. The present inventors found that the XRD obtained by this process did not show consistency in the ratio of the mixture of Form I and Form II.

U.S. Pat. Nos. 6,096,742 and 6,583,142 provides crystalline Form I and Form II of aprepitant, process for making these forms, pharmaceutical compositions comprising them and their method of use. These patents specifically claim aprepitant Form I, which is substantially free of Form II, and Form II which is substantially free of Form I of aprepitant.

Anal. Chem. (2003) 75:605-611, provides characterization and quantization of aprepitant polymorphs by Attenuated Total Reflectance Fourier Transform Infrared Spectroscopy.

Several processes have been reported for the preparation of aprepitant and various polymorphic forms for example in PCT Publication Nos. WO 2007/016582; WO 2007/039883; WO 2007/044829; WO 2007/088483; WO 2007/112457; WO 2007/147160; WO 2008/026216; WO 2008/044102; WO 2008/104512; WO 2009/001203.

There is a continuing interest in morphological forms among other properties. There is a need in the art for a process for producing crystalline aprepitant having Form I content in a consistent range. Extensive laboratory and full scale research has resulted a process for the preparation of crystalline aprepitant having not more than 15% by weight of Form I content, which is stable over the time and is suitable for formulating aprepitant.

SUMMARY OF THE INVENTION

The present invention provides a process for preparation of crystalline aprepitant having not more than 15% by weight of Form I content, which comprises:
 a) dissolving aprepitant in a suitable solvent,
 b) cooling the mixture to 10-15° C.,
 c) optionally seeding the solution with aprepitant Form I crystals,
 d) adding an anti-solvent to the solution, and
 e) isolating crystalline aprepitant having not more than 15% by weight of Form I content.

DETAILED DESCRIPTION OF THE INVENTION

In one aspect, the present invention provides a process for preparation of crystalline aprepitant having not more than 15% by weight of Form I content, which comprises:
 a) dissolving aprepitant in a suitable solvent to obtain a solution,
 b) cooling the solution to 10-15° C.,
 c) optionally seeding the solution with aprepitant Form I crystals,
 d) adding an anti-solvent to the solution, and
 e) isolating crystalline aprepitant having not more than 15% by weight of Form I content.

In step a) of the process of the present invention, a solution is obtained by dissolving aprepitant in a suitable solvent. Aprepitant prepared by any method known in the art can be used as starting material. Methods for preparing aprepitant are well known, e.g., U.S. Pat. Nos. 5,719,147 and 6,096,742. The starting material used for the processes of the present invention may be any crystalline or other form of aprepitant, including various solvates and hydrates. With crystallization processes, the crystalline form of the starting material generally does not affect the final result since the original crystalline form will change once in solution.

The term "suitable solvent" includes any solvent or solvent mixture in which aprepitant can be solubilized, including for example, esters, lower alkanols, halogenated hydrocarbons, ketones, ethers, polar aprotic solvents or mixtures thereof.

Examples of esters include ethyl acetate, n-propyl acetate, isopropyl acetate, n-butyl acetate and the like. Examples of lower alkanol solvents include methanol, ethanol, n-propanol, isopropanol, butanol and the like. Examples of halogenated hydrocarbons include dichloromethane, chloroform, 1,2-dichloroethane and the like. Examples of ketones include acetone, methyl ethyl ketone and the like. Examples of ethers include dimethyl ether, diethyl ether, diisoproyl ether tetrahydrofuran, methyl tert butyl ether and the like. Examples of polar aprotic solvent include N,N-dimethylformamide, N,N-dimethylacetamide, dimethylsulphoxide, acetonitrile N-methylpyrrolidone and the like. Preferably, the solvent is a lower alkanol and most preferably the solvent is methanol.

The solution may be obtained by heating the aprepitant in a suitable solvent. The dissolution can be carried out at a temperature ranging from about 20° C. to about 65° C. Any other temperature is also acceptable as long as a clear solution of aprepitant is obtained. The amount of solvent used for dissolution depends on the solvent and the dissolution temperature adopted.

After the dissolution of aprepitant in the solvent, the solution may optionally be filtered in order to remove any extraneous matter present in the solution using any standard filtration techniques known in the art. If desired, a filtering aid such as celite can be added to the solution.

The Form I content in the final product vary depending on the crystallization temperature, crystallization time, and the duration of addition of anti-solvent.

In step b) the clear solution is initially cooled to about 30-35° C. in about 45 to 60 minutes and then further cooled to about 10-15° C. in about 45 to 60 minutes.

In step c) optionally small quantity of seed crystal of Form I may be added to the solution. In the present context, the term "small quantity" means 0.1 to 5 weight percent. The seed crystal of Form I may be prepared by any method known in the art e.g., U.S. Pat. No. 6,096,742.

In step d) an anti-solvent is added to the solution.

Suitable anti-solvents are water, alkanes, ethers, aromatic hydrocarbon and mixtures thereof. Examples of alkanes include hexane, heptane and the like. Examples of ethers include dimethyl ether, diethyl ether, diisoproyl ether tetrahydrofuran, methyl tert butyl ether and the like. Examples of aromatic hydrocarbon include toluene, p-xylene and the like. Preferably, the anti-solvent is water.

The anti-solvent may be pre-cooled to a temperature of about 8-10° C. The anti-solvent can be added at 10-15° C., preferably maintaining the temperature of the reaction mass in the range of 11-13° C. The anti-solvent can be added for a time period of about 50-75 minutes. This temperature range is critical to obtain crystalline aprepitant having not more than 15% by weight of Form I content.

In step e) crystalline aprepitant having not more than 15% by weight of Form I content is isolated from the reaction mixture. Crystalline aprepitant having not more than 15% by weight of Form I content can be isolated by various techniques known in the art.

The crystals so isolated can be washed with a solvent. The solvent used for washing may be a mixture of solvents comprising the solvent used in step a) for dissolution and the anti-solvent used in step d).

The isolated crystalline aprepitant having not more than 15% by weight of Form I content may be further dried. Drying can be carried out for example in a vacuum tray drier, air oven and the like. The drying can be carried out at temperatures of about 40-55° C. for a sufficient time period of about 10-12 hours.

The Form I content of crystalline aprepitant obtained by the process as described above is preferably between 6-18% by weight, and more preferably 10-14% by weight.

BRIEF DESCRIPTION OF THE DRAWINGS

FIG. 1a is a table listing the position and intensities of spectral features found in FIG. 1.

FIG. 2a is a table listing the position and intensities of spectral features found in FIG. 2.

Figure 1:
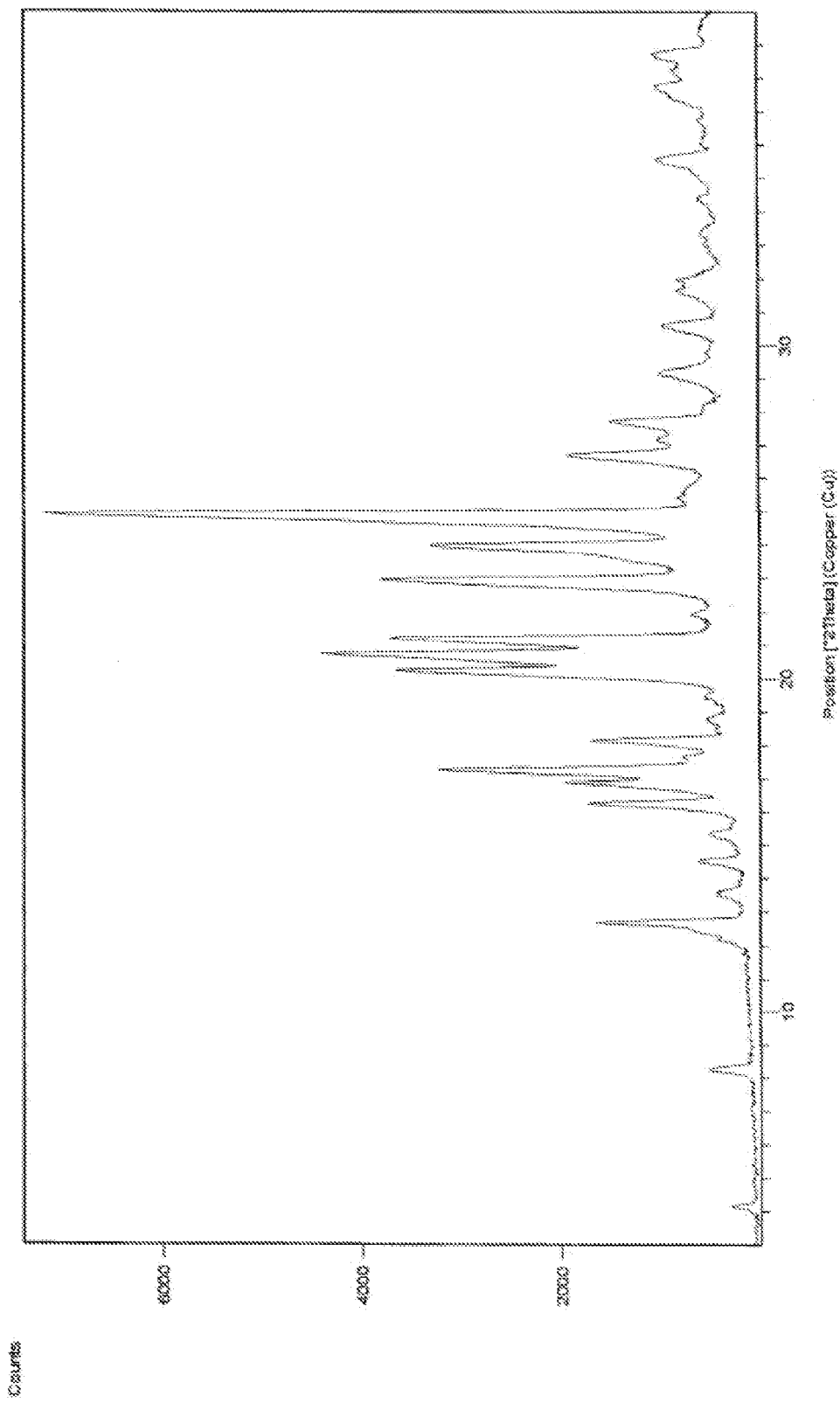
FIG. 1 depicts XRPD of crystalline aprepitant having not more than 15% by weight of Form I content, prepared according to Example 1.
Figure 2:
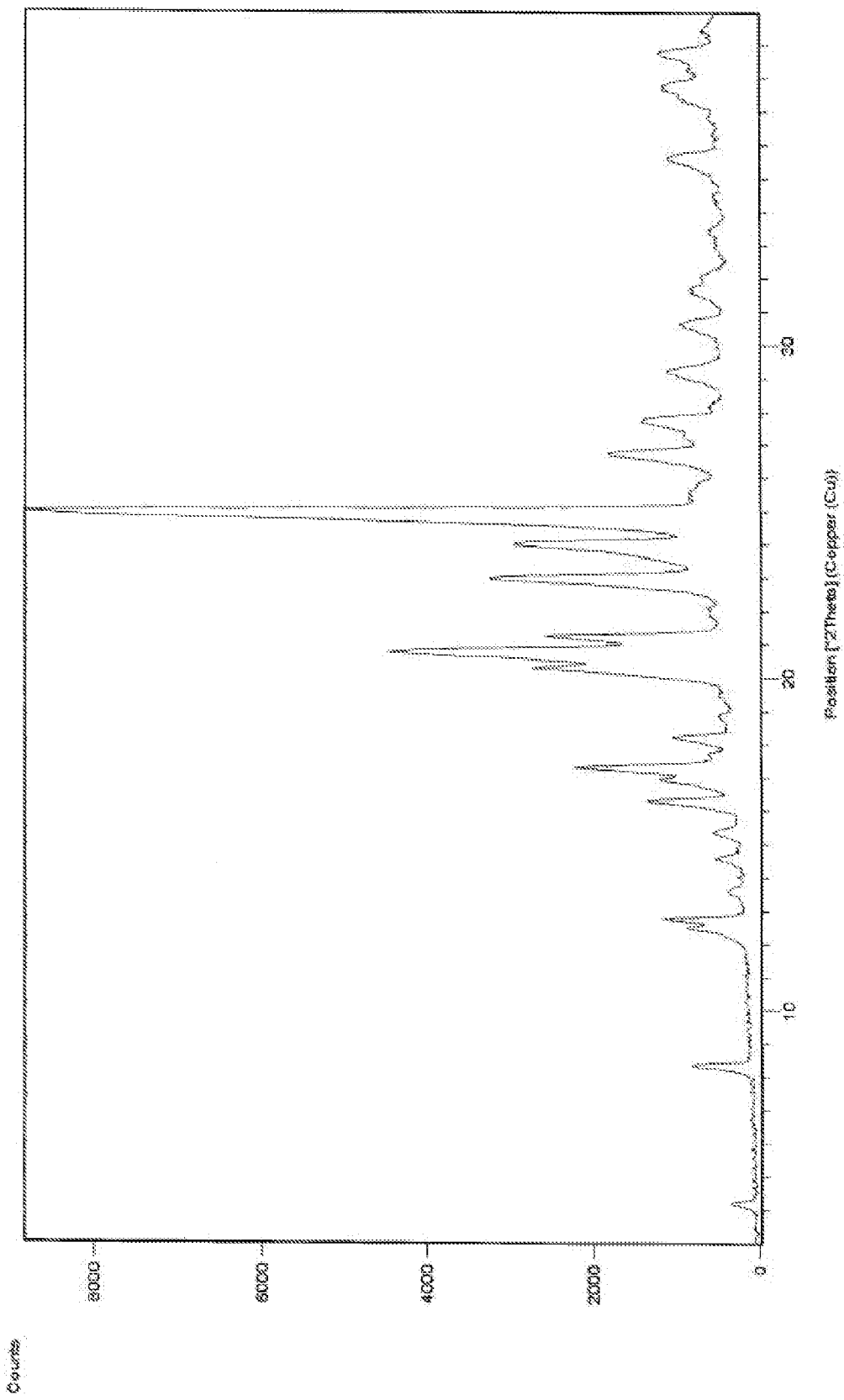
FIG. 2 depicts XRPD of crystalline aprepitant having not more than 15% by weight of Form I content, prepared according to Example 2.

Powder XRD of the samples were determined by using Instrument: Panalytical; Mode: Expert PRO; Detector: Xcelerator; ScanRange: 3-40; Step size: 0.02; Range: 3-40 degree 2 theta.

While the present invention has been described in terms of its specific embodiments, certain modifications and equivalents will be apparent to those skilled in the art and are intended to be included within the scope of the present invention.

EXAMPLES

Example 1

Preparation of Crystalline Aprepitant Having not More than 15% by Weight of Form I Content Aprepitant (200 g) and methanol (3000 ml) were charged at 25-30° C. and the mixture was heated to 60-65° C. and maintained for 30 minutes. The solution was cooled to 30° C. in about 50 minutes and then further cooled to 11° C. in about 50 minutes. Seed crystals of aprepitant (Form I) (0.5 g) was added to the solution. Pre-cooled water (1600 ml) (8-10° C.) was added in 60 minutes maintaining the temperature of reaction mass in the range of 11-13° C. The reaction mixture was stirred for 15 minutes. The solid was filtered and washed with methanol:water (2:1) mixture, suck dried for 15 minutes and further dried in vacuum tray drier at 48° C. for 10-12 hours to obtain the title compound.

Yield: 190 g

Content of Form I: 12.1% by weight.

Example 2

Preparation of Crystalline Aprepitant Having not More than 15% by Weight of Form I Content Aprepitant (200 g) and methanol (3000 ml) were charged at 25-30° C. and the mixture was heated to 60-65° C. and maintained for 30 minutes. The solution was cooled to 30° C. in about 50 minutes and then further cooled to 11° C. in about 50 minutes. Seed crystals of aprepitant (Form I) (0.5 g) was added to the solution. Pre-cooled water (1600 ml) (8-10° C.) was added in 60 minutes maintaining the temperature of reaction mass in the range of 11-13° C. The reaction mixture was stirred for 15 minutes. The solid was filtered and washed with methanol:water (2:1) mixture, suck dried for 15 minutes and further dried in vacuum tray drier at 48° C. for 10-12 hours to obtain the title compound.

Yield: 190 g

Content of Form I: 13.4% by weight.

The invention claimed is:

1. A process for preparation of crystalline aprepitant having not more than 15% by weight of Form I content which comprises:
   a) dissolving aprepitant in a suitable solvent to obtain a solution,
   b) cooling the solution to 10-15° C.,
   c) optionally seeding the solution with aprepitant Form I crystals,
   d) adding an anti-solvent to the solution, and
   e) isolating crystalline aprepitant having not more than 15% by weight of Form I content.

2. A process according to claim 1, wherein the dissolution in step a) is carried out at a temperature ranging from about 20° C. to about 65° C.

3. A process according to claim 1, wherein suitable solvent is selected from the group consisting of esters, lower alkanols, halogenated hydrocarbons, ketones, ethers, polar aprotic solvents or mixtures thereof.

4. A process according to claim 3, wherein the suitable solvent is methanol.

5. A process according to claim 1, wherein the solution obtained in step a) is initially cooled to about 30° C. to about 35° C. in about 45 minutes to about 60 minutes.

6. A process according to claim 5, wherein the solution obtained in step a) is further cooled to 10° C. to 15° C. in about 45 minutes to about 60 minutes.

7. A process according to claim 1, wherein the solution is seeded with aprepitant Form I crystals, prior to adding an anti-solvent.

8. A process according to claim 7, wherein seeding is between about 0.1 and about 5% by weight of aprepitant Form I.

9. A process according to claim 1, wherein the anti-solvent is selected from the group consisting of water, alkanes, ethers, aromatic hydrocarbon or mixtures thereof.

10. A process according to claim 8, wherein the anti-solvent is water.

11. A process according to claim 1, wherein the anti-solvent is pre-cooled to a temperature of about 8° C. to about 15° C.

12. A process according to claim 1, wherein the anti-solvent is added to the solution at a temperature of 10° C. to 15° C.

13. A process according to claim 1, wherein the anti-solvent is added to the solution at a temperature of 11° C. to 13° C.

14. A process according to claim 1, wherein the anti-solvent is added to the solution for a time period of about 50 to about 75 minutes.

* * * * *

UNITED STATES PATENT AND TRADEMARK OFFICE
CERTIFICATE OF CORRECTION

PATENT NO. : 8,816,072 B2  Page 1 of 1
APPLICATION NO. : 13/375548
DATED : August 26, 2014
INVENTOR(S) : Deepak Mohanlal Jain et al.

It is certified that error appears in the above-identified patent and that said Letters Patent is hereby corrected as shown below:

In the Specification

COLUMN 1, LINES 14-17:

"5-[[(2R,3S)-2-[(1R)-[3,5-bis(trifluoromethyl)phenyl]ethoxy]-3-(4-fluorophenyl)-4-morpholinyl]methyl]-1,2-dihydro-3H-1,2,4-triazol-3-one"

should read

-- 5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one --

Signed and Sealed this
Twenty-ninth Day of September, 2015

Michelle K. Lee
*Director of the United States Patent and Trademark Office*